United States Patent
Von Maydell

(10) Patent No.: US 9,207,057 B2
(45) Date of Patent: Dec. 8, 2015

(54) DEVICE FOR HEIGHT MEASUREMENT HAVING A HEADPIECE

(75) Inventor: Marc-Oliver Von Maydell, Hamburg (DE)

(73) Assignee: SECA AG, Reinach BL (CH)

( * ) Notice: Subject to any disclaimer, the term of this patent is extended or adjusted under 35 U.S.C. 154(b) by 120 days.

(21) Appl. No.: 13/990,207

(22) PCT Filed: Sep. 5, 2011

(86) PCT No.: PCT/DE2011/001726
§ 371 (c)(1),
(2), (4) Date: May 29, 2013

(87) PCT Pub. No.: WO2012/092910
PCT Pub. Date: Jul. 12, 2012

(65) Prior Publication Data
US 2013/0263461 A1   Oct. 10, 2013

(30) Foreign Application Priority Data
Nov. 30, 2010   (DE) .......................... 10 2010 054 023

(51) Int. Cl.
*G01B 3/06*   (2006.01)
*A61B 5/107*   (2006.01)
*G01B 3/00*   (2006.01)

(52) U.S. Cl.
CPC .............. *G01B 3/002* (2013.01); *A61B 5/1072* (2013.01)

(58) Field of Classification Search
CPC ............................... G01B 3/002; A61B 5/1072
USPC ..................................... 33/512, 465, 478, 832
See application file for complete search history.

(56) References Cited

U.S. PATENT DOCUMENTS

| | | | | | |
|---|---|---|---|---|---|
| 1,158,508 | A | * | 11/1915 | Kramer | 33/478 |
| 1,359,758 | A | * | 11/1920 | Slavik | 403/92 |
| 1,549,151 | A | * | 8/1925 | Rasmussen | 33/478 |
| 1,860,184 | A | * | 5/1932 | Jacobs | 33/512 |
| 1,996,553 | A | * | 4/1935 | Scully | 33/512 |
| 2,965,970 | A | * | 12/1960 | Rocheleau | 33/832 |
| 4,134,212 | A | * | 1/1979 | Allen | 33/512 |
| 4,495,702 | A | | 1/1985 | Bergstedt | |
| 5,357,683 | A | * | 10/1994 | Trevino | 33/528 |
| 6,073,359 | A | * | 6/2000 | Lee | 33/759 |
| 6,128,824 | A | * | 10/2000 | Yang | 33/511 |
| 6,643,942 | B1 | * | 11/2003 | Russell | 33/459 |
| 6,646,209 | B2 | * | 11/2003 | Montagnino et al. | 177/126 |
| 6,807,743 | B2 | * | 10/2004 | Odachowski | 33/465 |
| 8,109,008 | B1 | * | 2/2012 | Niemczak et al. | 33/832 |
| 2005/0155246 | A1 | | 7/2005 | Montagnino | |
| 2008/0244921 | A1 | * | 10/2008 | Silberman et al. | 33/832 |

FOREIGN PATENT DOCUMENTS

DE   19808432   9/1999
DE   202005003048 Y   7/2006

* cited by examiner

*Primary Examiner* — Christopher Fulton
(74) *Attorney, Agent, or Firm* — Lucas & Mercanti, LLP; Klaus P. Stoffel

(57) ABSTRACT

A device for measuring the height of persons, the device including a vertical element and a headpiece arranged on the vertical element so as to be freely positionable. The headpiece is arranged so that it is rotatable relative to the vertical element by a rotational joint. An axis of rotation of the rotational joint is arranged obliquely with respect to a longitudinal axis of the vertical element.

5 Claims, 2 Drawing Sheets

DEVICE FOR HEIGHT MEASUREMENT HAVING A HEADPIECE

The present application is a 371 of International application PCT/DE2011/001726, filed Sep. 5, 2011, which claims priority of DE 10 2010 054 023.4, filed Nov. 30, 2010, the priority of these applications is hereby claimed and these applications are incorporated herein by reference.

BACKGROUND OF THE INVENTION

The invention relates to a device for height measurement of persons, wherein the device includes a vertical element and a head stop positionally arranged at the vertical element, wherein the head stop is arranged so as to be rotatable relative to the vertical element via a rotary joint.

Devices of this type are typically constructed as so-called height measuring rods. The height measuring rods can be self-supporting by using a leg. Such height measuring rods can also be mounted at a support structure, for example, a wall or a scale.

A head stop is used for pre-setting a defined positioning of a person to be measured and for reinforcing a determination of the measurement result. The head stop can be slidable along a vertical element of the device, or may be positioned by moveable segments of a vertical element. For example, DE 198 08 432 describes positioning such a head stop with the use of telescoping segments of the vertical element.

In a state of use, the head stop extends essentially at a right angle to the vertical element. For facilitating a compact stowing of the device, the head stop can also be arranged so as to be pivotable relative to the vertical element. However, an upward or downward pivoting of the head stop typically causes impairment of the person to be measured.

SUMMARY OF THE INVENTION

It is the object of the present invention to construct a device of the type mentioned in the introduction in such a way that a pivotable arrangement of the vertical element is achieved without impairing the comfort of the user.

In accordance with the invention, this object is met in that an axis of rotation of the rotary joint is arranged inclined relative to a longitudinal axis of the vertical element.

By arranging the axis of rotation of the rotary element inclined relative to the longitudinal axis of the vertical element, it is possible, when carrying out the pivoting movement, to avoid a movement component of the head stop in the direction toward the user, or to limit the movement component to a spatially small area. Consequently, in comparison to using a horizontally extending axis of rotation, it is not necessary that the user has to avoid the head stop when the pivoting movement is carried out.

A curved path of movement for the head stop can be provided, especially by having the axis of rotation extend inclined relative to a horizontal direction.

A typical embodiment is made available if the axis of rotation includes an angle of inclination of about 45 degrees relative to the horizontal direction.

A simple and robust construction is achieved if the rotary joint includes one pinion as well as two surfaces of rotation.

An advantageous structural configuration resides in that one surface of rotation is connected to the vertical element and the other surface of rotation is connected to the head stop.

An advantageous spatial orientation resides in that the rotary surfaces extend essentially transversely to the axis of rotation.

For reinforcing a space saving transport of the device, it is proposed that the head stop extends with a longitudinal axis in a basic position essentially parallel to a longitudinal axis of the vertical element.

A precise and reproducible height measurement is reinforced if the head stop extends in a position of operation with a longitudinal axis essentially transversely of a longitudinal axis of the vertical element.

A preset positioning is reinforced in that a latching unit is used for at least one positioning of the head stop relative to the vertical element.

Also contributing to a compact configuration is the fact that the vertical element and/or the head stop are arranged so as to be telescoping.

BRIEF DESCRIPTION OF THE DRAWING

In the drawings, embodiments of the invention are schematically illustrated. In the drawings.

DETAILED DESCRIPTION OF THE INVENTION

Figure 1:
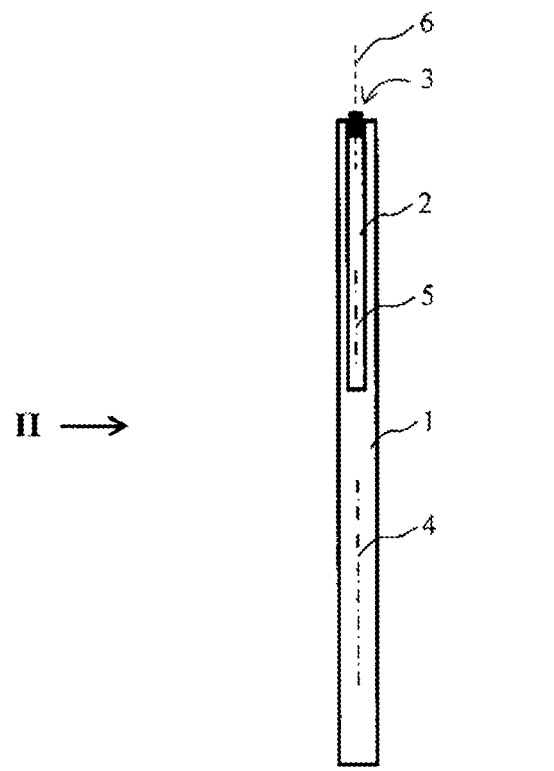
FIG. 1 is a front view of a height measuring rod with a pivotable head stop.

In accordance with the embodiment in FIG. 1, the device for height measurement includes a vertical element 1 which is movably connected to a head stop 2. The connection of the head stop 2 to the vertical element 1 is effected with the use of a pivoting joint 3. FIG. 1 shows the head stop 2 in a swung down position.

Figure 2:
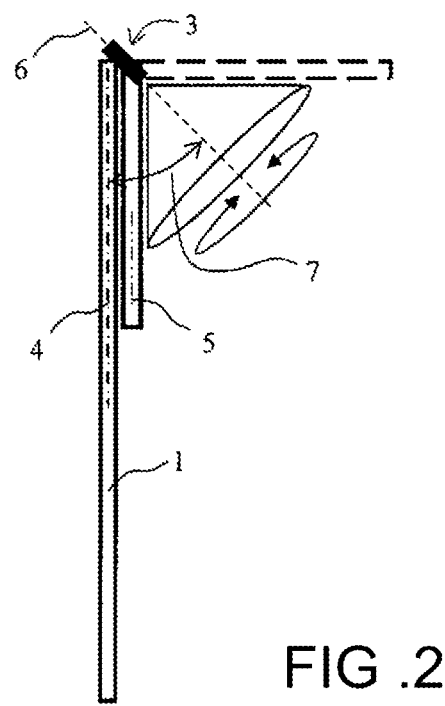
FIG. 2 is a side view in the viewing direction II in FIG. 1 with a positioning unit shown in broken lines in the upwardly swung position of the head stop.

FIG. 2 illustrates the construction according to FIG. 1 in a side view. It can be seen that, in this swung down position of the head stop 2, longitudinal axes 4, 5 of the vertical element 1, on the one hand, and the head stop 2, on the other hand, extend essentially parallel to each other. This supports a compact stowing. It can also be seen that an axis of rotation 6 of the pivoting joint 3 extends obliquely relative to the longitudinal axis 4 of the vertical element 1. In the illustrated embodiment, an angle of inclination 7 of the axis of rotation 6 relative to the longitudinal axis 4 is approximately 45 degrees. Starting from the vertical element 1, the axis of rotation 6 extends at a grade.

Figure 3:
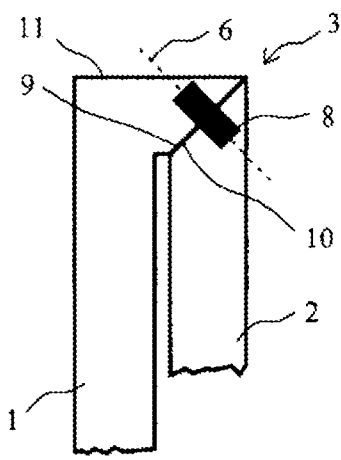
FIG. 3 shows an embodiment for realizing the pivoting joint.

FIG. 3 illustrates the construction of the pivoting joint 3 in more detail. In this case, the pivoting joint 3 consists of a pin 8 and two rotary surfaces 9, 10 which extend so as to face each other. The rotary surface 9 is in this case connected to the vertical element 1 and the rotary surface 10 is connected to the head stop 2.

In the illustrated embodiment, the rotary surfaces 9 and 10 are constructed so as to be plane and extend transversely of the axis of rotation 6. The pin 8 extends in the direction of the axis of rotation 6.

In accordance with the embodiment in FIG. 3, the vertical element 1 has a lateral projection 11 on which the rotary surface 9 is mounted.

Figure 4:
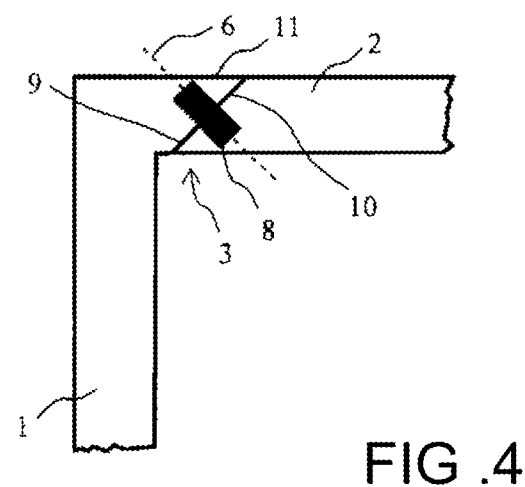
FIG. 4 shows the arrangement according to FIG. 3 with the head stop in an upwardly swung state.

FIG. 4 shows the arrangement according to FIG. 3 after the head stop 2 has been pivoted upwardly. This is effected by turning around the axis of rotation 6. When carrying out the rotary movement starting from the state of operation shown in FIG. 3, the head stop 2 initially carries out a lateral movement and is then transferred along a curved path of movement into the state of operation according to FIG. 4. The positioning according to FIG. 3 and/or according to FIG. 4 can be secured or predetermined by latching means.

The above described device for height measuring can be used as an individual unit or in combination with a scale for measuring the weight of a person. A determination of the height information can be carried out visually by reading a measurement scale or by measuring technology by using suitable sensors. The measured height information may be transferred to evaluating devices.

For example, the pivoting joint 3 can be fixedly connected to a telescoping vertical element 1. However, a movable arrangement on the vertical element 1 is also possible. For using the pivoting joint according to the invention, it is not required that the person to be measured leaves the area of the height measurement unit when the head stop is swung upwardly. Rather, the head stop carries out, during the upward pivoting movement, a circular segment-like movement around the head of the user.

As an alternative to the illustrated plane construction of the rotary surfaces 9, 10 it is, for example, also possible to use ring-like profilings which engage in each other, or spherically curved rotary surfaces 9, 10. Essential in all embodiments is the downwardly extending axis of rotation 6 starting from the vertical element 1.

The invention claimed is:

1. A device for measuring height of persons, comprising: a vertical element; and a head stop positionably arranged at the vertical element, wherein the head stop is arranged so as to be rotatable relative to the vertical element by a rotary joint, the rotary joint having an axis of rotation arranged obliquely relative to a longitudinal axis of the vertical element, wherein the axis of rotation extends inclined relative to a. horizontal direction, wherein the head stop has a longitudinal axis that extends in a basic position of the head stop substantially parallel to a longitudinal axis of the vertical element, wherein the head stop has a longitudinal axis that extends in a position of operation of the head stop substantially transversely of a longitudinal axis of the vertical element, wherein in both the basic position and the position of operation the head stop and the vertical element are in a common plane.

2. The device according to claim 1, wherein the axis of rotation extends at an angle of inclination of about 45 degrees relative to the horizontal direction.

3. The device according to claim 1, wherein the rotary joint includes a pin and two rotary surfaces.

4. The device according to claim 3, wherein a first of the rotary surfaces is connected to the vertical element, and a second of the rotary surfaces is connected to the head stop.

5. The device according to claim 3, wherein the rotary surfaces extend essentially transversely of the axis of rotation.

* * * * *